(12) United States Patent
Iwai et al.

(10) Patent No.: US 9,624,263 B2
(45) Date of Patent: Apr. 18, 2017

(54) METHOD OF RECOVERING PEPTIDE AND METHOD OF DETECTING PEPTIDE

(71) Applicant: SYSMEX CORPORATION, Kobe-shi, Hyogo (JP)

(72) Inventors: Atsushi Iwai, Kobe (JP); Sanai Tsunokuni, Kobe (JP); Kana Kawasaki, Kobe (JP); Hiroyuki Kabata, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 302 days.

(21) Appl. No.: 14/601,388

(22) Filed: Jan. 21, 2015

(65) Prior Publication Data
US 2015/0210736 A1    Jul. 30, 2015

(30) Foreign Application Priority Data
Jan. 29, 2014    (JP) .................................. 2014-014517

(51) Int. Cl.
*C07K 1/34*  (2006.01)
*G01N 27/447* (2006.01)
*C07K 1/14*  (2006.01)

(52) U.S. Cl.
CPC .............. *C07K 1/34* (2013.01); *C07K 1/145* (2013.01); *G01N 27/44747* (2013.01)

(58) Field of Classification Search
None
See application file for complete search history.

(56) References Cited

U.S. PATENT DOCUMENTS

2012/0277407 A1* 11/2012 Yamamoto ............... C07K 1/34
530/344

OTHER PUBLICATIONS

Lowenthal et al. Clinical Chemistry. 51:10, 1933-1945 (2005).*
G-Biosciences. Protein Purification Handbood & Selection Guide. 2012.*
Mark S. Lowenthal et al., Analysis of Albumin-Associated Peptides and Proteins from Ovarian Cancer Patients, Clinical Chemistry, 2005, pp. 1933-1945, vol. 51, No. 10.

* cited by examiner

*Primary Examiner* — Amber D Steele
*Assistant Examiner* — Schuyler Milton
(74) *Attorney, Agent, or Firm* — Sughrue Mion, PLLC

(57) ABSTRACT

Disclosed is a method of recovering a peptide including: mixing a liquid sample containing a complex of peptide and protein in blood with a reagent containing at least one selected from the group consisting of $Zn^{2+}$, $Ca^{2+}$, $Li^+$, $Ba^{2+}$, $Mg^{2+}$, $Mn^{2+}$, and a metal compound that forms any of these metal ions to liberate the peptide from the protein in blood; and recovering the liberated peptide.

20 Claims, 1 Drawing Sheet

METHOD OF RECOVERING PEPTIDE AND METHOD OF DETECTING PEPTIDE

BACKGROUND OF THE INVENTION (1) Field of the Invention

The present invention relates to a method of recovering a peptide from a liquid sample such as blood, and a method of detecting a peptide from a liquid sample such as blood.

(2) Description of Related Art

There is a wide variety of peptides in blood. These peptides include peptides that indicate the differences in concentrations in blood between a living body with healthy and specific pathologic condition. Such peptides are useful as biomarkers for diseases in clinical test fields.

A protein such as albumin or globulin is contained in the blood (hereinafter also referred to as "protein in blood"). Peptides bind to the protein in blood in many cases. Therefore, in detection of peptides, it is preferable to liberate the peptides from the protein in blood. As a technique of liberating a peptide, there is a technique in US Patent Application Publication No. 2012/0277407, which is herein incorporated by reference. The method described in US Patent Application Publication No. 2012/0277407 is a method comprising heat-treating a solution containing a complex of peptide and albumin to form a non-peptide binding self-aggregate of albumin and liberating the peptide from the albumin.

SUMMARY OF THE INVENTION

The scope of the present invention is defined solely by the appended claims, and is not affected to any degree by the statements within this summary.

As a result of intensive studies, the present inventors have found that peptides can be recovered or detected at a high recovery rate by mixing a liquid sample containing a complex of peptide and protein in blood with a reagent containing a specific metal ion or a metal compound that forms the metal ion.

Thus, the present invention provides a method of recovering a peptide comprising: liberating a peptide from a protein in blood by mixing a liquid sample containing a complex of the peptide and the protein in blood with a reagent containing at least one selected from the group consisting of $Zn^{2+}$, $Ca^{2+}$, $Li^+$, $Ba^{2+}$, $Mg^{2+}$, $Mn^{2+}$, and a metal compound that forms any of these metal ions; and recovering the liberated peptide.

The present invention also provides a method of detecting a peptide comprising: liberating a peptide from a protein in blood by mixing a liquid sample containing a complex of the peptide and the protein in blood with a reagent containing at least one selected from the group consisting of $Zn^{2+}$, $Ca^{2+}$, $Li^+$, $Ba^{2+}$, $Mg^{2+}$, $Mn^{2+}$, and a metal compound that forms any of these metal ions; and detecting the liberated peptide.

DETAILED DESCRIPTION OF THE PREFERRED EMBODIMENTS

Figure 1A:
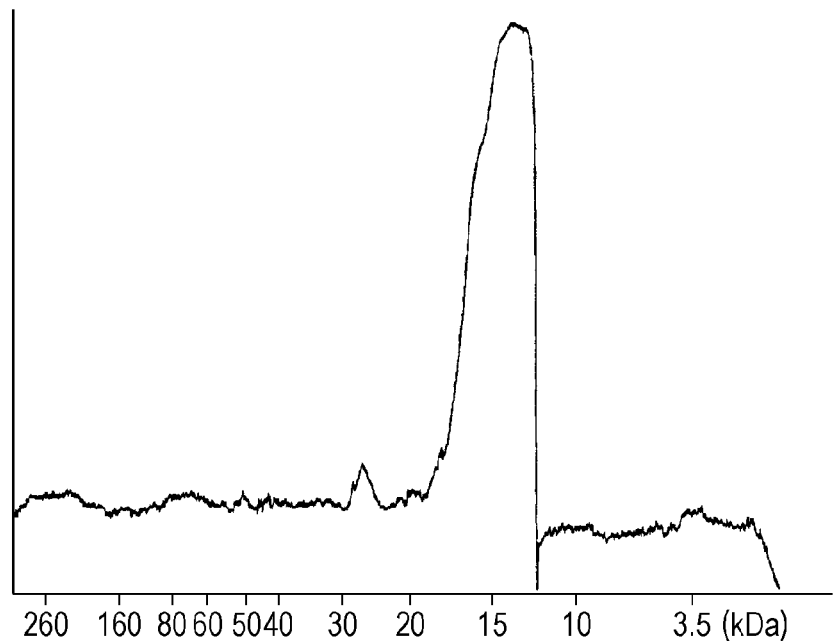
FIG. 1A is a graph showing the band intensity of SDS-PAGE gel.

The liberating step of the method of recovering a peptide of the present invention (hereinafter also simply referred to as "recovery method") is a step of mixing a liquid sample containing a complex of peptide and protein in blood with a reagent containing at least one selected from the group consisting of $Zn^{2+}$, $Ca^{2+}$, $Li^+$, $Ba^{2+}$, $Mg^{2+}$, $Mn^{2+}$, and a metal compound that forms any of these metal ions (hereinafter also referred to as "reagent") to liberate the peptide from the protein in blood.

In a preferred embodiment, the liquid sample is a biological sample. Examples of the biological sample include body fluid such as blood collected from a living body. Examples thereof also include plasma and serum obtained from blood. The liquid sample may be diluted for use. Those skilled in the art are able to set the dilution rate, as appropriate.

The "protein in blood" used herein means a protein present in the blood, such as albumin or globulin. The protein in blood binds to the peptide described below in blood to form a complex. The peptide is liberated through the liberating step of the embodiment of the present invention. The protein in blood after liberation of the peptide is aggregated and precipitated during the treatment in the liberating step.

In the embodiment, the peptide to be recovered is not particularly limited, and it may be a naturally occurring peptide or a synthetic peptide. The length of the peptide is not particularly limited as long as the peptide is recovered by the method of the present disclosure. A relatively large size of polypeptide (for example, the protein in blood) among polypeptides in the liquid sample is aggregated and precipitated by the treatment in the liberating step, meanwhile, a relatively small size of polypeptide (for example, oligopeptide) is liberated in the solution. The liberated polypeptide is a "peptide" that can be recovered by the method of the present disclosure. Not all the polypeptides in the liquid sample are precipitated or liberated completely. Depending on the polypeptides, some of the polypeptides are contained in precipitated aggregates and also are contained in a liberated component. Such polypeptides are contained in the liberated component (for example, supernatant) and they can be recovered. Thus, these polypeptides are included in the "peptide". According to the method of the present disclosure, when an amino acid is a peptide having about 130 residues, the amino acid is liberated in a sample. Accordingly, a peptide having less than 130 residues is suitable for recovery. However, the present invention is not limited thereto. When not only polypeptides originally present in a liquid sample but also polypeptides fragmented in the process of being treated by the method of the present disclosure are contained in the liberated component, these polypeptides are included in the "peptide".

In the embodiment, the isoelectric point of the peptide is not particularly limited. The peptide may be any of a basic peptide, an acidic peptide, and a neutral peptide.

In the embodiment, the peptide may be derived from molecules produced in a living body or may be derived from molecules introduced from outside a living body. Examples of the peptide derived from molecules produced in a living body include peptides produced in a living body and fragments of polypeptides produced in a living body.

In the embodiment, the peptide may be a biomarker present in the blood.

Examples of the peptide as the biomarker include ghrelin, brain natriuretic peptide (BNP), adrenocorticotropichormone (ACTH), atrial natriuretic peptide (ANP), bradykinin, α-endorphin, C-peptide, C3f fragment, ITIH4 fragment, and Aβ peptide. However, they are not limited thereto. That is, the peptide to be liberated can be one that has an unidentified novel sequence of amino acids.

When a biomarker is detected, the method of the embodiment of the present invention can be used to obtain, for example, information about the presence of a specific disease and the stage of progression of the disease. That is, it is assumed that information providing an indication of determining the presence of a disease or the stage of progression of the disease is obtained by recovering a peptide, biomarker from a biological sample by the method of the embodiment of the present invention, and detecting the recovered peptide qualitatively and/or quantitatively.

In the embodiment, the peptide may be a polypeptide administered into a living body, a metabolite thereof or a fragment of these polypeptides. In this case, the method of the embodiment of the present invention may be used to obtain information about drug susceptibility. That is, it is assumed that information providing an indication of determining the sensitivity of a drug is obtained by recovering a polypeptide, drug administered to a living body or a metabolite thereof by the method of the embodiment of the present invention and detecting the recovered peptide qualitatively and/or quantitatively.

In the embodiment, the peptide may be not a peptide derived from a living body being examined, but a peptide introduced into a living body from outside a living body. Examples thereof include peptides derived from pathogens (bacteria, viruses, etc.). In this case, the method of the embodiment of the present invention may be used to obtain information, for example, about infection by pathogens. That is, it is assumed that information providing an indication of determining the infection by pathogens is obtained by recovering a peptide derived from proteins including pathogens or a peptide derived from toxins produced by pathogens (for example, verotoxin) from a biological sample by the method of the embodiment of the present invention, and detecting the recovered peptide qualitatively and/or quantitatively.

In the embodiment, "the reagent" is not particularly limited as long as it is one containing the following metal ions or one containing a metal compound that dissolves in water or an aqueous medium to form any one of the following metal ions. The reagent may be in the form of a solid or liquid.

In the embodiment, the "metal ion" is selected from the group consisting of $Zn^{2+}$, $Ca^{2+}$, $Li^+$, $Ba^{2+}$, $Mg^{2+}$, and $Mn^{2+}$. Among them, $Zn^{2+}$, $Ca^{2+}$, $Li^+$, $Ba^{2+}$, and $Mg^{2+}$ are particularly preferred. As described above, these metal ions are formed into ion binding compounds, and the compounds in the form of ion are dissolved in a solid or a liquid-form solution so as to be contained in the reagent. For example, the above metal ions are formed into chlorides, bromides, and thiocyanates, and these preferably are solids. Particularly preferably, these ions in the form of $ZnCl_2$ or $CaCl_2$ are contained in the reagent.

In a case where the reagent is a solid, the reagent may be any of metal compounds capable of forming the metal ions listed above, may be a mixture of at least two of the metal compounds, or may further contain components other than the metal compounds listed above within an acceptable range to perform the present invention.

In a case where the reagent is in the form of liquid, the reagent is a solution containing at least one of the metal ions listed above and may further contain components other than the metal ions listed above within an acceptable range to perform the present invention. A solvent is not particularly limited as long as it is suitable for dissolving the metal compound, and those skilled in the art are able to select the solvent, as appropriate. Examples of the solvent include water and phosphate buffered saline (PBS).

In the embodiment, the additive amount of the reagent to the liquid sample is not particularly limited as long as it is an amount that the final concentration of metal ion is higher than the concentration of metal ion in the blood. Those skilled in the art are able to set the amount, as appropriate. The additive amount of metal ion is preferably an amount that the final concentration of metal ion is from 0.01 to 300 mM, preferably from 0.5 to 200 mM, still more preferably from 5 to 100 mM.

In a preferred embodiment, the recovery method of the present invention further comprises heat-treating a mixture obtained by mixing a liquid sample with a reagent. The temperature and time for heat-treatment of the mixture are preferably set in the range in which peptides in the mixture are not completely denatured by heat. The term "peptides are completely denatured" used herein means that peptides are denatured to the extent that the peptides cannot be detected.

Those skilled in the art are able to set the heating temperature, as appropriate. The heat treatment is performed preferably at a temperature of 40° C. or more and 200° C. or less, more preferably a temperature of 50° C. or more and 180° C. or less, still more preferably a temperature of 65° C. or more and 160° C. or less.

Those skilled in the art are able to set the heating time, as appropriate. The heat treatment time is preferably from 30 seconds to 5 minutes, more preferably from 1 minute to 3 minutes.

The rate of temperature increase in the heat treatment is not particularly limited and those skilled in the art are able to set the rate, as appropriate.

In the embodiment, the method of heat treatment is not particularly limited as long as it is a method capable of heating the mixture at the temperatures described above. The method may be selected from known methods in the art. Examples of the method include a method of external heating by conduction and a method of heating by microwaves.

In the embodiment, the apparatus of heat-treatment is not particularly limited as long as it is an apparatus which heats the mixture at controlled temperatures. A hydrothermal reaction vessel and a microwave irradiation device are used, for example.

A precipitate considered to be a self-aggregate of protein in blood is formed from a complex of peptide and protein in blood in the mixture in the above manner. US Patent Application Publication No. 2012/0277407 has reported that almost all the molecules of the self-aggregate of albumin lose the ability to bind to peptides due to denaturation of higher order structure of albumin upon heat treatment. Consequently, the present invention is not intended to be restricted to a certain theory. A hypothesis capable of explaining the mechanism of the recovery method of the present disclosure is concerned that the peptide is liberated from the protein in blood upon the formation of the precipitate considered to be a self-aggregate of protein in blood in the recovery method of the present invention.

The precipitate is insoluble in a solvent contained in the mixture, and the precipitate is formed in the heat-treated mixture. That is, the heat-treated mixture is divided into two fractions: the precipitate considered to be a self-aggregate of protein in blood and supernatant containing peptides.

In the embodiment, the peptide liberated from protein in blood is able to be identified as the expected free form in the supernatant fraction using any known method in the art. Examples of the method include electrophoresis and mass spectrometry.

In the recovering step of the recovery method of the present disclosure, the method of removing the precipitate from the heat-treated mixture is not particularly limited. For example, the precipitate may be directly removed using a spatula. Alternatively, the precipitate may be removed using a commercially available separator or filter paper. Thus, in the recovery method of the present disclosure, peptides can be recovered by removing the precipitate from the heat-treated mixture and obtaining the supernatant fraction containing the liberated peptides.

As described above, the self-aggregate of albumin is not bound to the peptide. Therefore, it is unlikely that the precipitate considered to be a self-aggregate of the protein in blood which contains albumin as a main component binds to the peptide. However, the precipitate has water absorbability like a sponge and adsorbs a part of the supernatant containing peptides.

Therefore, the recovery method of the present disclosure may further include a step of obtaining the supernatant containing peptides from the removed precipitate. In the step of obtaining the supernatant containing peptides from the precipitate, for example, the precipitate is transferred into a tube with ultrafilter and centrifuged to squeeze the supernatant out. Alternatively, the supernatant may be obtained by stirring the precipitate with a homogenizer. The step of obtaining the supernatant containing peptides from the precipitate needs no heat treatment.

In order to remove the protein in blood, a method has been conventionally performed in which the blood sample is passed through a column adsorbing specifically albumin, albumin in the blood sample remains on the column, and a liberating form of peptides in the blood are collected. However, the report by Lowenthal et al. (Clin. Chem., vol. 51, 1933-1945 (2005)) has showed that 98% of peptides in serum are bound to albumin. That is, according to the method of the embodiment of the present invention, the peptides are also removed together with the albumin by the method of adsorbing albumin and removing peptides. Consequently, only a very small amount of the peptides are obtained.

According to the embodiment of the present invention, the peptides bound to the protein in blood such as albumin are liberated and then recovered, whereby peptides can be more efficiently recovered.

The present disclosure also includes a method of detecting a peptide. According to the detection method, the peptides liberated by the above liberating step are detected by any conventionally known method. The detection includes quantitative detection, qualitative detection, and semi-qualitative detection (determination of negativity, weak positivity or strong positivity).

The results obtained by the detection method are used to obtain information such as determination of the diseases, drug susceptibility or the presence or absence of infection.

Hereinafter, the present disclosure will be described in detail with reference to Examples, however the present disclosure is not limited thereto.

EXAMPLES

Example 1

(1) Preparation of Liquid Sample Containing Complex of Peptide and Protein in Blood ACTH partial peptide consisting of 1st to 24th amino acids of ACTH and TMR-ACTH partial peptide in which the above peptide was labeled with tetramethyl rhodamine (TMR) (a red fluorescent dye) (Biologica Co, Ltd.) were used as peptides. The ACTH is a basic peptide (isoelectric point pI=10.64). Whole blood of healthy subject (ProMed which was purchased from Dx LLC) was added to a tris phosphoric acid buffer (Tris-HCl [pH=7.0] (final concentration: 100 mM)), sodium phosphate (final concentration: 0.4 mM), and NaCl (final concentration: 6 mM) at a final concentration of ACTH partial peptide of 5 μM to prepare a liquid sample containing a complex of peptide and protein in blood.

(2) Heat-Treatment of Liquid Sample Containing Complex of Peptide and Protein in Blood Various metal ions were added to the liquid sample containing a complex of the peptide and protein in blood at a final concentration of 100 mM. Thus, a mixture containing a complex of peptide and protein in blood and metal ions was obtained. The used metal compounds forming various metal ions are as follows: $ZnCl_2$ (manufactured by NACALAI TESQUE, INC., product No. 36920-24, product name: zinc chloride, special grade); $CaCl_2$ (manufactured by Wako Pure Chemical Industries, Ltd., product No. 039-00431, product name: calcium chloride dihydrate, special grade); LiCl (manufactured by Wako Pure Chemical Industries, Ltd., product No. 125-01161, product name: lithium chloride, special grade); $BaCl_2$ (manufactured by Wako Pure Chemical Industries, Ltd., product No. 127-00171, product name: barium chloride dihydrate, special grade); $MgCl_2$ (manufactured by Wako Pure Chemical Industries, Ltd., product No. 131-00162, product name: magnesium chloride hexahydrate, special grade); $MnCl_2$ (manufactured by Wako Pure Chemical Industries, Ltd., product No. 139-00722, product name: manganese chloride (II) tetrahydrate, special grade); $SrCl_2$ (manufactured by Wako Pure Chemical Industries, Ltd., product No. 195-07361, product name: strontium chloride hexahydrate, atom); CsCl (manufactured by Wako Pure Chemical Industries, Ltd., product No. 034-08161, product name: cesium chloride for equilibrium density gradient centrifugation); and $CoCl_2$ (manufactured by Wako Pure Chemical Industries, Ltd., product No. 036-03682, product name: cobalt chloride hexahydrate, special grade).

The resultant mixture (1.4 mL) was transferred to a 10-mL volume glass test tube. The tube was sealed with a pressure resistant sealing holder for test tube of Teflon (Milestone General K.K.) and placed in a microwave applicator (MultiSYNTH type, Milestone General K.K.). Then, heat treatment was performed by increasing the temperature from room temperature (25° C.) to 100° C. for 30 seconds and then increasing the temperature from 100° C. to 160° C. for 1 minute. Cooling after heating was performed by blowing compressed air to the pressure resistant sealing holder from an air compressor (YC-3 R type, YAEZAKI KUATU CO., LTD.) connected to the microwave applicator. The cooling rate was set to 20° C./min. The liquid sample (1.4 mL) not containing metal ions was used as a control. The liquid sample was similarly sealed and subjected to the same heat-treatment. Precipitates were observed in all of the heat-treated mixtures and liquid sample.

(3) Detection of Peptide and Protein in Blood

The supernatant fractions of the heat-treated mixtures and the heat-treated liquid sample were used as samples and SDS-PAGE was performed on the samples. Specifically, a sample buffer (not containing a reductant) prepared by mixing a 10× loading buffer (TAKARA BIO INC.) with a 60% (w/w) glycerol solution at a ratio of 1:1 was mixed with each of the samples. Then, electrophoresis was performed on each of the resultant mixtures at 200 V (constant voltage) for 30 minutes using NuPAGE 4-12% Bis-Tris Gel and NuPAGE MES SDS Running Buffer (both products are manufactured by Life Technologies Corporation). The used electrophoresis tank was X-Cell Sure Lock Minicell (Life Technologies Corporation.) and the used electric power unit was Power Station 1000XP (ATTO Corporation). As for the gel after electrophoresis, the TMR-ACTH partial peptide was detected using a fluorescence imager (Pharos FX Molecular Imager type, Bio-Rad Laboratories, Inc.). On the basis of the results of fluorescent imaging, the densitometry value of the peptide or protein residue was calculated using image processing software ImageJ 1.46r (NIH). The recovery rate was calculated according to Equation 1 below.

Recovery rate=(densitometry value when adding metal ions (after hydrothermal reaction))/(densitometry value when not adding metal ions (after hydrothermal reaction))      Equation 1

As for the "recovery rate" in examples after the present Examples, because of a significant effect of the present invention compared to the conventional technique of performing hydrothermal reaction and recovering peptides without adding metal ions, as described in Equation 1, the ratio between the densitometry value in the case of using a measurement sample after the treatment of the present Examples (hydrothermal reaction and addition of metal ions) and the densitometry value in the case of using a measurement sample as a control (measurement sample subjected to hydrothermal treatment without adding metal ions, i.e., the conventional technique) was used. Therefore, the "recovery rate" is represented as a relative value when the measurement sample as a control is defined as 1.

The band of peptide in the case of adding metal ions to be detected in fluorescence imaging is expected to be stronger than the band of peptide in the case of not adding metal ions. Accordingly, the densitometry value in the peptide band region in the case of adding metal ions is expected to be larger than the densitometry value in the band region in the case of not adding metal ions. Consequently, the recovery rate calculated by Equation 1 is considered to increase when peptides can be recovered at an excellent recovery rate.

The results are shown in Table 1 below.

TABLE 1

| Types of metal ions | Recovery rate |
| --- | --- |
| Without additives (after hydrothermal reaction) | 1.00 |
| $Zn^{2+}$ | 3.80 |
| $Ca^{2+}$ | 1.59 |
| $Li^+$ | 1.35 |
| $Ba^{2+}$ | 1.64 |
| $Mg^{2+}$ | 1.37 |
| $Mn^{2+}$ | 1.27 |
| $Sr^{2+}$ | 0.73 |
| $Cs^+$ | 0.88 |
| $Co^{2+}$ | 0.09 |

As a result, in the case of adding $Zn^{2+}$, $Ca^{2+}$, $Li^+$, $Ba^{2+}$, $Mg^{2+}$ or $Mn^{2+}$, the recovery rate of peptide increased, compared to the case of not adding metal ions. On the other hand, even when $Sr^{2+}$, $Cs^+$ or $Co^{2+}$ was added, an increase in the recovery rate was not observed.

This result shows that in the case of adding $Zn^{2+}$, $Ca^{2+}$, $Li^+$, $Ba^{2+}$, $Mg^{2+}$ or $Mn^{2+}$ as a metal ion, a large amount of peptides can be recovered, compared to the case of not adding any of the metal ions.

Example 2

The present inventors evaluated the recovery rate of peptide in the same manner as Example 1 except that 237th to 249th fragments of HSA fluorescently labeled with TMR (isoelectric point pI=12.01, sequence: AWAVARLSQRFPK, length of amino acid residues: 13) and BNP fluorescently labeled with TMR (isoelectric point pI=10.95) were used in addition to TMR-ACTH partial peptide in order to examine whether an improvement in recovery rate of peptide was observed even when peptides having different isoelectric points (pI) were used in the recovery method of the present invention. In the present Examples, $Zn^{2+}$ was used as a metal ion. The results are shown in Tables 2 to 4 below. In Tables 2 to 4, the recovery rate is a recovery rate in a case where the densitometry result of each band region obtained by performing SDS-PAGE using only the various peptides as samples is defined as 1.

TABLE 2

237th to 249th fragments of HSA

| Addition of $Zn^{2+}$ | Recovery rate |
| --- | --- |
| Not added | 1.00 |
| Added | 3.59 |

TABLE 3

BNP

| Addition of $Zn^{2+}$ | Recovery rate |
| --- | --- |
| Not added | 1.00 |
| Added | 1.78 |

TABLE 4

ACTH (1-24)

| Addition of $Zn^{2+}$ | Recovery rate |
| --- | --- |
| Not added | 1.00 |
| Added | 3.80 |

As a result, an excellent recovery rate of peptide was obtained as follows:

The recovery rate of 237th to 249th fragments of HSA in the case of using $Zn^{2+}$ ion increased by 3.59 times, compared to the case of not adding $Zn^{2+}$ ion. The recovery rate of BNP in the case of using $Zn^{2+}$ ion increased by 1.78 times, compared to the case of not adding $Zn^{2+}$ ion. The recovery rate of ACTH partial peptide in the case of using $Zn^{2+}$ ion increased by 3.80 times, compared to the case of not adding $Zn^{2+}$ ion.

The result shows that peptides having various isoelectric points can be recovered at an excellent recovery rate by the recovery method of the present invention.

Example 3

It was examined whether an improvement in recovery rate of peptide due to addition of metal ions was observed even when the heating temperature was changed in the same manner as Example 2 except that TMR-ACTH partial peptide was used as a peptide, heating by microwave irradiation was performed by increasing the temperature to each temperature in one stage, and each temperature was maintained for 20 seconds. The non-heated sample was left alone at room temperature. The results are shown in Table 5 below.

TABLE 5

| Experimental conditions | Recovery rate |
|---|---|
| Without addition of $Zn^{2+}$, without heat-treatment | 1.00 |
| Addition of $Zn^{2+}$, without heat-treatment | 1.63 |
| Addition of $Zn^{2+}$, heating at 65° C. | 1.52 |
| Addition of $Zn^{2+}$, heating at 120° C. | 2.63 |
| Addition of $Zn^{2+}$, heating at 160° C. | 2.08 |

As a result, in the case of adding $Zn^{2+}$ and not performing heat-treatment, the recovery rate of peptide excellently increased by 1.63 times, compared to the recovery rate of peptide in the case of not adding $Zn^{2+}$ and not performing heat-treatment. In the case of increasing the temperature to 65° C., 120° C. or 160° C. in the heat-treatment step, the recovery rate of peptide increased by 1.52 times, 2.63 times, and 2.08 times, respectively, compared to the recovery rate of peptide in the case of not adding $Zn^{2+}$ and not performing heat-treatment.

The result shows that peptides can be recovered at an excellent recovery rate in a wide range of temperatures.

As a result, in the case of adding $Zn^{2+}$ and not performing heat-treatment, the recovery rate of peptide excellently increased by 1.63 times, compared to the recovery rate of peptide in the case of not adding $Zn^{2+}$ and not performing heat-treatment. In the case of increasing the temperature to 65° C., 120° C. or 160° C. in the heat-treatment step, the recovery rate of peptide increased by 1.52 times, 2.63 times, and 2.08 times, respectively, compared to the recovery rate of peptide in the case of not adding $Zn^{2+}$ and not performing heat-treatment.

The result shows that peptides can be recovered at an excellent recovery rate in a wide range of temperatures.

Example 4~9

The present inventors performed the experiments described in Examples 4 to 9 below in order to evaluate impacts of differences in concentrations of metal ions or liquid samples on the recovery rate of peptide.

Example 4

(1) Preparation of Liquid Sample Containing Complex of Peptide and Protein in Blood Whole blood was 3-fold diluted with the tris phosphoric acid buffer. The TMR-ACTH partial peptide was added to the resultant diluted solution at a final concentration of 2 µM to prepare a liquid sample containing a complex of peptide and protein in blood.

(2) Heat-Treatment of Liquid Sample Containing Complex of Peptide and Protein in Blood $ZnCl_2$ (manufactured by NACALAI TESQUE, INC., product No. 36920-24, product name: zinc chloride, special grade) was added to the liquid sample containing a complex of peptide and protein in blood at a final concentration of $Zn^{2+}$ of 100 mM to prepare a mixture containing a complex of peptide and protein in blood and $Zn^{2+}$.

The resultant mixture (1.4 mL) was transferred to a 10-mL volume glass test tube. The tube was sealed with a pressure resistant sealing holder for test tube of Teflon (Milestone General K.K.) and placed in a microwave applicator (MultiSYNTH type, Milestone General K.K.). Then, heat treatment was performed by increasing the temperature from room temperature (25° C.) to 100° C. for 30 seconds and then increasing the temperature from 100° C. to 160° C. for 1 minute. Cooling after heating was performed by blowing compressed air to the pressure resistant sealing holder from an air compressor (YC-3 R type, YAEZAKI KUATU. CO., LTD.) connected to the microwave applicator. The cooling rate was set to 20° C./min. As a control, the liquid sample (1.4 ml) not containing $Zn^{2+}$ was similarly sealed and subjected to the same heat-treatment. The recovery rate obtained by using the liquid sample was defined as 1. Precipitates were observed in all of the heat-treated mixtures and liquid sample.

(3) Detection of Peptide and Protein in Blood

The supernatant fractions of the heat-treated mixtures and the heat-treated liquid sample were used as samples and SDS-PAGE was performed on the samples. Specifically, a sample buffer (not containing a reductant) prepared by mixing a 10× loading buffer (TAKARA BIO INC.) with a 60% (w/w) glycerol solution at a ratio of 1:1 was mixed with each of the samples. Then, electrophoresis was performed on each of the resultant mixtures at 200 V (constant voltage) for 30 minutes using NuPAGE 4-12% Bis-Tris Gel and NuPAGE MES SDS Running Buffer (both products are manufactured by Life Technologies Corporation). The used electrophoresis tank was X-Cell Sure Lock Minicell (Life Technologies Corporation.) and the used electric power unit was Power Station 1000XP (ATTO Corporation). As for the gel after electrophoresis, the TMR-ACTH partial peptide was detected using a fluorescence imager (Pharos FX Molecular Imager type, Bio-Rad Laboratories, Inc.). On the basis of the results of fluorescent imaging, the recovery rate was calculated according to Equation 1 above.

The results are shown in Table 6 below. As is clear from the description of Table 6, the recovery rate of $Zn^{2+}$ at a final concentration of 100 mM calculated by converting to the numerical value in a case where the recovery rate (at a final concentration of 0 mM) when not adding $Zn^{2+}$ is defined as 1 is shown.

TABLE 6

| Final concentration of $Zn^{2+}$ | Recovery rate |
|---|---|
| 0 mM | 1.00 |
| 100 mM | 1.97 |

As a result, in the case of setting the final concentration of $Zn^{2+}$ to 100 mM, peptides could be recovered excellently at a recovery rate 1.97 times, compared to that in the case of setting the final concentration of $Zn^{2+}$ to 0 mM.

This result shows that peptides can be recovered at an excellent recovery rate from the protein in blood even when the diluted whole blood is used as the liquid sample containing a complex of peptide and protein in blood.

Example 5

The results of fluorescence imaging were obtained in the same manner as Example 4 except that the dilution rate of whole blood was set to 5 times. On the basis of the results, the recovery rate was calculated according to Equation 1 above.

The results are shown in Table 7 below. As is clear from the description of Table 7, the recovery rate of $Zn^{2+}$ at a final concentration of 100 mM calculated by converting to the numerical value in a case where the recovery rate (at a final concentration of 0 mM) when not adding $Zn^{2+}$ is defined as 1 is shown.

TABLE 7

| Final concentration of $Zn^{2+}$ | Recovery rate |
| --- | --- |
| 0 mM | 1.00 |
| 100 mM | 2.17 |

As a result, in the case of setting the final concentration of $Zn^{2+}$ to 100 mM, peptides could be recovered excellently at a recovery rate 2.17 times, compared to that in the case of setting the final concentration of $Zn^{2+}$ to 0 mM.

This result shows that peptides can be recovered at an excellent recovery rate from the protein in blood even when the whole blood used as the liquid sample containing a complex of peptide and protein in blood was diluted.

The results of Examples 1, 2, 4 and 5 show that peptides can be recovered at an excellent recovery rate from the protein in blood even when the whole blood diluted at various rates is used as the liquid sample containing a complex of peptide and protein in blood.

Example 6

The results of fluorescence imaging were obtained in the same manner as Example 4 except that the undiluted serum was used as the liquid sample containing a complex of peptide and protein in blood, and $Zn^{2+}$ was added or not added at a final concentration of 5 mM or 100 mM. On the basis of the results, the recovery rate was calculated according to Equation 1 above.

The results are shown in Table 8 below. As is clear from the description of Table 8, the recovery rate of $Zn^{2+}$ at a final concentration of 5 mM or 100 mM calculated by converting to the numerical value in a case where the recovery rate (at a final concentration of 0 mM) when not adding $Zn^{2+}$ is defined as 1 is shown.

TABLE 8

| Final concentration of $Zn^{2+}$ | Recovery rate |
| --- | --- |
| 0 mM | 1.00 |
| 5 mM | 3.02 |
| 100 mM | 6.85 |

As a result, in the case of setting the final concentration of $Zn^{2+}$ to 5 mM and 100 mM, respectively, peptides could be recovered excellently at recovery rates 3.02 times and 6.85 times, respectively, compared to the recovery rate in the case of setting the final concentration of $Zn^{2+}$ to 0 mM.

This result shows that peptides can be recovered at an excellent recovery rate from the protein in blood even when the serum is used as the liquid sample containing a complex of peptide and protein in blood.

Example 7

The results of fluorescence imaging were obtained in the same manner as Example 6 except that the serum used as the liquid sample containing a complex of peptide and protein in blood was 10-fold diluted, and $Zn^{2+}$ was added or not added at a final concentration of 100 mM. On the basis of the results, the recovery rate was calculated according to Equation 1 above.

The results are shown in Table 9 below. As is clear from the description of Table 9, the recovery rate of $Zn^{2+}$ at a final concentration of 100 mM calculated by converting to the numerical value in a case where the recovery rate of $Zn^{2+}$ at a final concentration of 0 mM is defined as 1 is shown.

TABLE 9

| Final concentration of $Zn^{2+}$ | Recovery rate |
| --- | --- |
| 0 mM | 1.00 |
| 100 mM | 1.35 |

As a result, in the case of setting the final concentration of $Zn^{2+}$ to 100 mM, peptides could be recovered excellently at a recovery rate 1.35 times, compared to that in the case of setting the final concentration of $Zn^{2+}$ to 0 mM.

This result shows that peptides can be recovered at an excellent recovery rate from the protein in blood even when the serum used as the liquid sample containing a complex of peptide and protein in blood is diluted.

Example 8

The results of fluorescence imaging were obtained in the same manner as Example 4 except that the undiluted serum was used as the liquid sample containing a complex of peptide and protein in blood, and $Ca^{2+}$ was added or not added at a final concentration of 1000 mM as a metal ion. On the basis of the results, the recovery rate was calculated according to Equation 1 above.

The results are shown in Table 10 below. As is clear from the description of Table 10, the recovery rate of $Ca^{2+}$ at a final concentration of 1000 mM calculated by converting to the numerical value in a case where the recovery rate of $Ca^{2+}$ at a final concentration of 0 mM is defined as 1 is shown.

TABLE 10

| Final concentration of $Ca^{2+}$ | Recovery rate |
| --- | --- |
| 0 mM | 1.00 |
| 1000 mM | 1.45 |

As a result, in the case of setting the final concentration of $Ca^{2+}$ to 1000 mM, peptides could be recovered excellently at a recovery rate 1.45 times, compared to that in the case of setting the final concentration of $Ca^{2+}$ to 0 mM.

This result shows that peptides can be recovered at an excellent recovery rate from the protein in blood even when $Ca^{2+}$ is used as a metal ion.

Example 9

The results of fluorescence imaging were obtained in the same manner as Example 8 except that the serum used as the liquid sample containing a complex of peptide and protein in blood was 10-fold diluted. On the basis of the results, the recovery rate was calculated according to Equation 1 above.

The results are shown in Table 11 below. As is clear from the description of Table 11, the recovery rate of $Ca^{2+}$ at a final concentration of 1000 mM calculated by converting to the numerical value in a case where the recovery rate of $Ca^{2+}$ at a final concentration of 0 mM is defined as 1 is shown.

TABLE 11

| Final concentration of $Ca^{2+}$ | Recovery rate |
|---|---|
| 0 mM | 1.00 |
| 1000 mM | 1.39 |

As a result, in the case of setting the final concentration of $Ca^{2+}$ to 1000 mM, peptides could be recovered excellently at a recovery rate 1.39 times, compared to that in the case of setting the final concentration of $Ca^{2+}$ to 0 mM.

This result shows that peptides can be recovered at an excellent recovery rate from the protein in blood even when the serum used as the liquid sample is diluted in the case of using $Ca^{2+}$ as a metal ion.

Example 10

A tris phosphoric acid buffer, human serum γ-globulin (Wako Pure Chemical Industries, Ltd., product No. 071-02293), human serum albumin (Wako Pure Chemical Industries, Ltd., product No. 019-10503), and TMR-ACTH partial peptide (Biologica Co, Ltd.) were used to prepare a liquid sample. The final concentration of TMR-ACTH partial peptide was 2 μM, the final concentration of γ-globulin was 0 mg/mL or 4 mg/mL (0 μM or 25 μM when converted to an average molecular weight of 160 kDa), and the final concentration of human serum albumin was 0 μM or 120 μM. This liquid sample was mixed with a $ZnCl_2$-containing reagent at a final concentration of $ZnCl_2$ of 0 mM or 100 mM.

The liquid sample was allowed to stand at room temperature (25° C.) for 1.5 minutes or heated to 160° C., similarly to Example 1. As shown in Table 12, the liquid sample not containing any of γ-globulin, albumin, and $Zn^{2+}$ which had been allowed to stand at room temperature was designated as a control sample 1, the liquid sample not containing any of γ-globulin, albumin, and $Zn^{2+}$ which had been heated to 160° C. was designated as a control sample 2, and the liquid sample containing γ-globulin and albumin, but not containing $Zn^{2+}$ which had been allowed to stand at room temperature was designated as a control sample 3. The liquid sample containing all of γ-globulin, albumin, and $Zn^{2+}$ which had been allowed to stand at room temperature was designated as a measurement sample 1. The liquid sample containing all of γ-globulin, albumin, and $Zn^{2+}$ which had been heated to 160° C. was designated as a measurement sample 2.

TABLE 12

| | Structural component of each liquid sample | Heat-treatment |
|---|---|---|
| Control sample 1 | γ-globulin 0 mg/mL<br>Albumin 0 μM<br>$Zn^{2+}$ 0 mM | Allowed to stand at 25° C. |
| Control sample 2 | γ-globulin 0 mg/mL<br>Albumin 0 μM<br>$Zn^{2+}$ 0 mM | Heating at 160° C. |
| Control sample 3 | γ-globulin 4 mg/mL<br>Albumin 120 μM<br>$Zn^{2+}$ 0 mM | Allowed to stand at 25° C. |
| Measurement sample 1 | γ-globulin 4 mg/mL<br>Albumin 120 μM<br>$Zn^{2+}$ 100 mM | Allowed to stand at 25° C. |
| Measurement sample 2 | γ-globulin 4 mg/mL<br>Albumin 120 μM<br>$Zn^{2+}$ 100 mM | Heating at 160° C. |

The amounts of liberated TMR-ACTH partial peptide and complexed TMR-ACTH partial peptide in the liquid sample were determined by fluorescence polarization spectroscopy using the F-7000 type spectrophotofluorometer (manufactured by Hitachi High-Technologies Corporation). Specifically, aliquot of 600 μL was isolated from each control sample or each measurement sample and transferred to a fluorescent cell (optical path length 10 mm), followed by irradiation with excitation light having a wavelength of 550 nm (through a 5 nm band pass filter). The resultant fluorescent light from TMR-ACTH partial peptide (through a band pass filter of 5 nm at a photomultiplier tube applied-voltage of 400 V) was monitored, and the intensity of the fluorescent light at a wavelength of 580 nm was recorded. On the basis of the intensity, the ratio (the liberation amount) of ACTH partial peptide kept in a liberated state without binding to γ-globulin or albumin to form a complex was calculated according to Equation 2 below. As for TMR-ACTH partial peptide, a difference between the liberated state and the complexed state can be easily determined according to the size of the fluorescence intensity from TMR. Specifically, this is based on the phenomena that the TMR group of TMR-ACTH partial peptide in a complexed state tends to show a strong fluorescence (the peripheral environment of TMR is a protein component and it is hydrophobic), meanwhile, the TMR group of TMR-ACTH partial peptide in a liberated state tends to disappear (the peripheral environment of TMR is bulk water and it is hydrophilic).

Liberation amount=[(fluorescence intensity value of measurement sample)−(fluorescence intensity value of control sample 3)]/[(fluorescence intensity value of control sample 1)−(fluorescence intensity value of control sample 3)]   Equation 2

The results are shown in Table 13 below. In Table 12, the "liberation amount of peptide" in each liquid sample is a relative amount in each liquid sample in a case where the liberation amount when using the liquid sample not containing γ-globulin and albumin is defined as 1.

TABLE 13

| Sample | Liberation amount of peptide (or amount of first addition of peptide to sample) |
|---|---|
| Control sample 1 | 1.00 |
| Control sample 2 | 1.00 |
| Control sample 3 | 0.00 |
| Measurement sample 1 | 0.71 |
| Measurement sample 2 | 0.43 |

In Table 13, in the case of the liquid sample allowed to stand at room temperature (25° C.) in the absence of $Zn^{2+}$, the peptide was not liberated due to the formation of a complex of albumin and γ-globulin. On the other hand, in the case of adding 100 mM of $Zn^{2+}$ and being allowed to stand at room temperature, 70 percent of peptides could be recovered. In the case of adding 100 mM of $Zn^{2+}$ and heating to 160° C., 40 percent or more of peptides could be recovered.

The results show that when using $Zn^{2+}$ as a metal ion, peptides can be recovered at an excellent recovery rate from albumin and γ-globulin.

Example 11

As the peptide to be recovered, hen egg-white lysozyme hydrochloride having 129 residues (Wako 120-02674 Lot LAQ6504; about 15 kDa) was used. The lysozyme was dissolved in PBS. A $ZnCl_2$ solution was added to the resultant mixture to prepare a measurement sample 3. The concentration of lysozyme in the measurement sample 1 was 10 mg/mL, and the concentration of the $ZnCl_2$ solution was 0.1 M. A solution (without hydrothermal treatment) prepared by mixing the measurement sample 3, a tris phosphoric acid buffer (Tris.HCl [pH=7.0] (final concentration: 100 mM)), sodium phosphate (final concentration: 0.4 mM), and NaCl (final concentration: 6 mM) in an equivalent amount was used, and SDS-PAGE was performed on the solution. A graph of the band intensity of the gel is shown in FIG. 1A. The measurement sample 1 (1.4 mL) was transferred to a 10-mL volume vial, and the hydrothermal reaction was performed on the sample in the same manner as Example 1. A solution prepared by mixing the measurement sample 1 after the hydrothermal reaction, the tris phosphoric acid buffer, sodium phosphate, and NaCl in an equivalent amount was used, and SDS-PAGE was performed on the solution. A graph of the band intensity of the gel is shown in FIG. 1B.

In FIG. 1A, a large peak was observed at a position of 15 kDa. This corresponds to the size of the lysozyme dissolved in the sample. In FIG. 1B, a peak can be confirmed at a position of 15 kDa. However, the peak decreased greatly, compared to the peak of the PBS solution of lysozyme (FIG. 1A). In contrast, peaks were detected at a position of 3.5 to 10 kDa and a position of less than 3.5 kDa. This suggests that the lysozyme was fragmented. The peak at around 260 kDa is considered to be caused by lysozyme fragment aggregation.

Figure 1B:
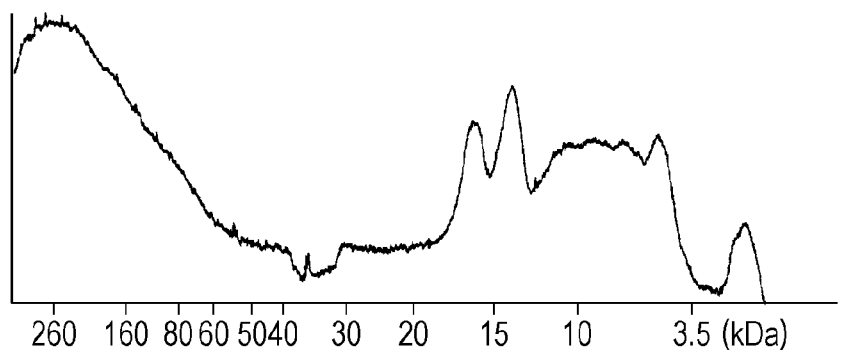
FIG. 1B is a graph showing the band intensity of SDS-PAGE gel.

The results of FIG. 1B show that when the method of recovering a peptide of the present invention is used, the lysozyme itself can be recovered and the fragment of the lysozyme can also be recovered.

What is claimed is:

1. A method of recovering a peptide, comprising:
   liberating a peptide from a protein in blood by mixing a liquid sample containing a complex of the peptide and the protein in blood with a reagent containing at least one selected from the group consisting of $Zn^{2+}$, $Ca^{2+}$, $Li^+$, $Ba^{2+}$, $Mg^{2+}$, $Mn^{2+}$, and a metal compound that forms any of these metal ions; and
   recovering the liberated peptide.

2. The method according to claim 1, wherein the liberating step comprises comprising a step of heat-treating a mixture of the liquid sample and the reagent.

3. The method according to claim 2, wherein the heat-treating is performed under the conditions where the peptide in the liquid sample is not completely denatured by heat.

4. The method according to claim 2, wherein the heat-treating is performed by irradiation with microwaves.

5. The method according to claim 4, wherein the mixture is heated to the range of 40° C. or higher and 120° C. or lower in the heat-treating.

6. The method according to claim 5, wherein the mixture is heated to the range of 30 seconds or longer and 5 minutes or shorter in the heat-treating.

7. The method according to claim 1, further comprising:
   removing a precipitate comprising the protein in blood which is formed after the mixing and before the recovering.

8. The method according to claim 2, further comprising:
   removing a precipitate comprising the protein in blood which is formed after the mixing and before the recovering.

9. The method according to claim 1, wherein the liquid sample is blood, plasma or serum.

10. The method according to claim 1, wherein the peptide is a peptide produced in a living body or a fragment thereof.

11. A method of detecting a peptide, comprising:
    liberating a peptide from a protein in blood by mixing a liquid sample containing a complex of the peptide and the protein in blood with a reagent containing at least one selected from the group consisting of $Zn^{2+}$, $Ca^{2+}$, $Li^+$, $Ba^{2+}$, $Mg^{2+}$, $Mn^{2+}$, and a metal compound that forms any of these metal ions; and
    detecting the liberated peptide.

12. The method according to claim 11, wherein the liberating step comprises comprising a step of heat-treating a mixture of the liquid sample and the reagent.

13. The method according to claim 12, wherein the heat-treating is performed under the conditions where the peptide in the liquid sample is not completely denatured by heat.

14. The method according to claim 12, wherein the heat-treating is performed by irradiation with microwaves.

15. The method according to claim 14, wherein the mixture is heated to the range of 40° C. or higher and 120° C. or lower in the heat-treating.

16. The method according to claim 15, wherein the mixture is heated to the range of 30 seconds or longer and 5 minutes or shorter in the heat-treating.

17. The method according to claim 11, further comprising:
    removing a precipitate comprising the protein in blood which is formed after the mixing and before the recovering.

18. The method according to claim 12, further comprising: removing a precipitate comprising the protein in blood which is formed after the mixing and before the recovering.

19. The method according to claim 11, wherein the liquid sample is blood, plasma or serum.

20. A method of detecting a peptide, comprising:
    liberating a peptide from a protein in blood by (1) mixing a liquid sample containing a complex of the peptide and the protein in blood with a reagent containing at least one selected from the group consisting of $Zn^{2+}$, $Ca^{2+}$, $Li^+$, $Ba^{2+}$, $Mg^{2+}$, $Mn^{2+}$, and a metal compound that forms any of these metal ions, and (ii) heating the mixture of the liquid sample and the reagent to the range of 40° C. or higher and 120° C. or lower; and
    recovering the liberated peptide; and
    detecting the recovered peptide.

* * * * *